United States Patent [19]

Chauvin et al.

[11] Patent Number: 5,449,852
[45] Date of Patent: Sep. 12, 1995

[54] PROCESS FOR THE METATHESIS OF OLEFINS WITH AN IMPROVED RHENIUM CATALYST

[75] Inventors: Yves Chauvin, Rueil Malmaison; Dominique Commereuc, Meudon, both of France

[73] Assignee: Institut Francais Du Petrole, Rueil Malmaison, France

[21] Appl. No.: 293,194

[22] Filed: Aug. 19, 1994

[30] Foreign Application Priority Data

Aug. 20, 1993 [FR] France ............................... 93 10196

[51] Int. Cl.$^6$ .................................................. C07C 6/04
[52] U.S. Cl. ......................................... 585/647; 585/643
[58] Field of Search ........................ 585/647, 470, 708

[56] References Cited

U.S. PATENT DOCUMENTS

| | | | |
|---|---|---|---|
| 3,642,931 | 2/1972 | Turner et al. | 260/683 D |
| 3,968,180 | 7/1976 | Kupper et al. | 260/666 A |
| 3,974,231 | 8/1976 | Küepper et al. | 260/666 A |
| 4,016,220 | 4/1977 | Küpper et al. | 260/683 D |
| 4,036,858 | 7/1977 | Küpper et al. | 260/348.5 L |
| 4,104,318 | 8/1978 | Hupp et al. | 260/669 A |
| 4,117,021 | 9/1978 | Hupp et al. | 260/669 A |

FOREIGN PATENT DOCUMENTS 1490277 8/1966 France .
1516853 12/1966 France .

*Primary Examiner*—Asok Pal
*Assistant Examiner*—Bekir L. Yildirim
*Attorney, Agent, or Firm*—Millen, White, Zelano & Branigan

[57] ABSTRACT

A process for the metathesis of olefins, wherein the olefins are reacted in contact with an improved catalyst comprising a niobium and/or tantalum compound and a rhenium compound on a porous support containing at least 75% alumina and having a surface area of at least 10 m$^2$/g.

16 Claims, No Drawings

PROCESS FOR THE METATHESIS OF OLEFINS WITH AN IMPROVED RHENIUM CATALYST

BACKGROUND OF THE INVENTION

The present invention relates to a process for the metathesis of olefins using an improved catalyst with a rhenium base.

The metathesis of olefins, or reaction redistributing alkylidene groups, is very useful in practice, e.g. for re-balancing the light olefins which result from steam cracking, olefins such as ethylene, propylene and butenes.

Various types of catalysts are capable of being used in the metathesis reaction: either homogeneous ones with constituent elements which are all soluble in the reaction medium, or heterogeneous ones which at least one element which is insoluble in said medium. These latter are particularly worthwhile when the active metal is costly and when it is necessary to envisage its reuse without any waste. This is the case for catalysts with a rhenium base, use of which in heterogeneous form has been recommended for catalysing the metathesis of simple olefins, e.g. in U.S. Pat. Nos. 3,641,189 and 3,676,520.

These catalysts have been prepared in the prior art by introducing rhenium oxide, using methods conventional in heterogeneous catalysis, onto various supports as described in U.S. Pat. No. 3,642,931. for example. Of the various supports, alumina, or a support containing alumina, seems to have the most worthwhile properties for conferring good activity and good stability upon the catalyst.

Numerous modifications to the base catalyst constituted by rhenium on alumina have been described to improve its properties. Beneficial effects have thus been found by adding alkaline compounds or alkaline earth compounds (U.S. Pat. No. 3,594,440, U.S. Pat. No. 3,637,892), acid anions (U.S. Pat. No. 3,697,613), tin oxides (GB 1,377,161), boron oxide (U.S. Pat. No. 5,055,628), or rare earths elements (U.S. Pat. No. 3,728,414).

SUMMARY OF THE INVENTION

The invention describes a process which uses catalysts with a rhenium base which are more active than those according to the prior art. It has actually been found that by adding niobium compounds and/or tantalum compounds to the rhenium supported on alumina, or to a support containing at least 75% by weight of alumina, the activity of these catalysts is unexpectedly improved, which makes it possible for lower proportions of rhenium to be used for the same activity which is important in view of the cost of this metal.

This effect is all the more surprising since similar solids which comprise niobium and/or tantalum compounds which are supported on alumina or on a support containing at least 75% by weight of alumina, but which have no rhenium, are not active as catalysts in the metathesis reaction.

The catalyst used in the process according to the invention therefore comprises at least three components: a porous support of alumina or a composite containing at least 75% by weight of alumina, 0.01 to 30% by weight of niobium and/or tantalum in oxide form, and 0.01 to 20% by weight of rhenium in oxide form.

The porous support is of alumina or a composite containing at least 75% by weight alumina which advantageously must have a surface area of appreciable size, e.g. at least 10 $m^2/g$, and preferably at least 50 $m^2/g$, and an adequate pore volume, e.g. at least 0.1 ml/g, and preferably 0.3–1 ml/g. Advantageously, an alumina of the same type as those types of catalysts used fop catalytic reforming can be used. Cubic gamma and eta forms are thus preferred.

The niobium and/or tantalum compound is of a halide or an oxyhalide (e.g. pentachloride or oxytrichloride), an alkoxide (e.g. pentaethoxide), or preferably a hydrated oxide placed in aqueous solution by the addition of a complexing agent such as oxalic acid and/or alcohol acids, particularly tartaric acid, or their ammonium salts. The niobium and/or tantalum compound can be introduced onto the support using any of the methods conventional for heterogeneous catalysis, e.g. by impregnation in solution. Usually, it is preferable to use the dry impregnation method, also known as capillary impregnation. The niobium and/or tantalum compound is placed in solution in water or in an organic solvent, e.g. an alcohol. The volume of solution is less than, or at the most equal to, the pore volume of the support. The amount of niobium and/or tantalum on the support is governed by the selection of the concentration of the impregnation solution. When the amount to be impregnated is greater than that which is permitted by a solution at its saturation limit, the operation has to be carried out several times with intermediate drying operations to eliminate the impregnation solvent, at a temperature of 90° to 250° C., for example, preferably of 100° to 180° C. This makes it possible for 0.01 to 30%, preferably 1 to 20%, and still more advantageously 2 to 12% by dry weight of niobium and/or tantalum to be introduced.

The preferred rhenium compounds are rhenium heptoxide, ammonium perrhenate and perrhenic acid. The rhenium compound can be introduced onto the support by sublimation in vapor phase or by impregnation in solution, for example. Usually, it is preferable to use the dry impregnation method described hereinabove where the rhenium compound is placed in aqueous solution or in an organic solution, e.g. a hydrocarbon, an alcohol or an ether. The amount of rhenium on the support is governed by the selection of the concentration of the impregnation solution. When the amount of rhenium to be impregnated is greater than that which is permitted by a solution at its saturation limit, the operation has to be carried out a number of times with intermediate drying operations to eliminate the impregnation solvent, at a temperature of 90° to 250° C., for example, preferably 100° to 180° C. This makes it possible for 0.01 to 20%, preferably 0.1 to 15%, and still more advantageously 0.5 to 8% by dry weight rhenium to be introduced.

The order in which the components: niobium and/or tantalum and rhenium are introduced onto the support is not critical. However, it is preferable to first of all introduce the niobium and/or tantalum and then the rhenium. After each impregnation stage, a drying operation is carried out at a temperature of 90° to 250° C., for example, preferably 100° to 180° C., and then calcination is carried out at a temperature of 250° to 700°, for example, preferably 300° to 600° C.

The catalyst can advantageously contain in addition to niobium and/or tantalum and rhenium, at least one alkali compound or alkaline-earth compounds which can preferably be added to the catalyst obtained following the steps previously described. These compounds can be present in variable proportions, usually from 0.01 to 20% and preferably from 0.05 to 10% by weight, and they can be introduced from precursors and using methods well-known to those skilled in the art.

The catalytic composition obtained following the above steps is activated by heating to between 400° and 1000° C., preferably between 500° and 900° C. The heating is done in a non-reducing gas atmosphere, for example: oxygen, nitrogen or argon, oxygen diluted by nitrogen, preferably in air, under static or dynamic conditions, a slight gaseous current being preferable, however. The humidity of the gaseous current is preferably kept to less than 200 ppm (parts per million). However, it is possible to carry out the heating in an atmosphere of the combustion gases of methane or a natural gas in the presence of an excess of air. This activation treatment lasts from 10 minutes to 5 hours or more, for example, after which time the active catalyst thus obtained is cooled in an atmosphere which is preferably anhydrous. It is advantageously possible to carry out purging in nitrogen, if necessary, before contact is made with the hydrocarbon charge.

The olefins capable of reacting during metathesis in the presence of the catalyst based on supported rhenium, described hereinabove, can be linear olefins which correspond to the general formula: $R_1R_2C=CR_3R_4$ where $R_1$, $R_2$, $R_3$ and $R_4$ which can be identical or different are hydrogen or a hydrocarbyl radical with 1 to 20 carbon atoms. The olefins can also be cyclic in structure, the ring comprising 3 to 20 carbon atoms. It is either possible to react an olefin with itself or to react a number of olefins mixed together. One application example is the production of propylene by reacting ethylene with 2-butenes, or the inverse transformation reaction of propylene into a mixture of ethylene and 2-butenes.

The metathesis reaction is carried out preferably in the absence of a solvent. However, the presence of a solvent such as a hydrocarbon, or a halogenated, aliphatic, cycloalkane or aromatic hydrocarbon is not harmful.

The reaction can be carried out batchwise in an agitated reactor, or continuously, by passing the reagent(s) through a fixed bed, a mobile bed or a fluidised bed, of the catalyst.

The metathesis reaction is carried out in the gaseous phase or in the liquid phase. Usually, it is preferable to operate in the liquid phase, in the absence of oxygen and humidity. The reagents and solvents are usefully treated for this purpose beforehand.

The pressure at which the reaction is carried out is not critical. However, for an operation in the liquid phase, it is necessary to maintain a pressure which is at least equal to the vapor pressure of the reaction medium at the reaction temperature. The operation most frequently takes place at a temperature of between 0° and 200° C., preferably between 20° and 150° C.

EXAMPLES

The following examples illustrate the invention, without limiting the scope thereof.

EXAMPLE 1

Preparation of the Catalyst 8.55 g of a cubic gamma alumina with a specific surface area of 184 m$^2$/g and a pore volume of 0.67 ml/g is calcined at 300° C. in air. After cooling at ambient temperature, this alumina is impregnated with a 2.51 g solution of pentaethoxyniobium in 4 ml anhydrous ethanol. After 30 minutes of contact at ambient temperature, the solid obtained is dried in a drying oven at 120° C. for one night. It is then calcined in a current of air, at about 20 l/h, at a temperature of 500° C. for 2 hours. A solution is prepared for impregnating the rhenium by diluting 0.23 ml of a concentrated aqueous solution of perrhenic acid containing 54.08% by Weight rhenium (specific mass: 2.417 g/ml) in 5 ml water. This solution is impregnated onto the solid which has previously been calcined. After 30 minutes of contact at ambient temperature, the solid obtained is dried in a drying oven at 120° C. for one night. It is then calcined in a current of air (about 20 l/h), dried by passing through a molecular sieve bed, at a temperature of 550° C. for 2 hours. During the subsequent cooling period, a current of dry nitrogen is substituted for the current of air. 10 g of activated catalyst is thus obtained which is kept in a dry and inert atmosphere prior to use. Its content of niobium oxide is 10.5 % by weight and its content of rhenium metal is 3% by weight.

Use in Metathesis

The 10 g of catalyst prepared above are charged, protected from air and humidity, into a reactor constituted by a stainless steel tube provided with a double casing with water circulating to enable the temperature to be regulated. Liquid propylene is injected through the bottom of the reactor using a pump, at a flow rate of 43.8 g/h. The temperature is regulated at 35° C. and the pressure is kept at 3.5 MPa using a regulator which is placed downstream of the reactor. Under these conditions, 26.7% of the propylene issuing from the reactor is converted into an equimolar mixture of ethylene and 2-butenes.

EXAMPLE 2

Preparation of the Catalyst

An aqueous solution of oxalic acid is prepared by dissolving 46.8 g acid in 331.4 g distilled water. A gel of hydrated niobium oxide is prepared by hydrolysis of the niobium pentachloride in an aqueous solution of ammonia, followed by five washing operations with distilled water. 46.9 g of this hydrated gel is taken away and is dissolved in the aqueous solution of oxalic acid prepared above. 70g of a cubic gamma alumina with a specific surface area of 184 m$^2$/g and a pore volume of 0.67 ml/g is calcined at 300° C. in air. After cooling at ambient temperature, this alumina is impregnated with 42 ml of the oxalic solution of the niobium oxide gel prepared above. After 30 minutes of contact at ambient temperature the solid obtained is dried in a drying oven at 120° C. This impregnation operation followed by the drying operation is repeated nine times, after which time the solid obtained is calcined in a current of air at about 20 l/h at a temperature of 500° C. for 2 hours. Its content of niobium oxide is 9.6 % by weight. 9.61 g of this solid is taken which is impregnated with a solution prepared by diluting 0.23 ml of a concentrated aqueous solution of perrhenic acid containing 54.08% by weight rhenium (specific mass: 2.417 g/ml) in 5 ml water. After 30 minutes of contact at ambient temperature, the solid obtained is dried in a drying oven at 120° C. for one night. It is then calcined in a current of air (about 20 l/h), dried by passing through a molecular sieve bed at a temperature of 550° C. for 2 hours. During the subsequent cooling period, a current of dry nitrogen is substituted for the air current. Thus, 10 g of activated catalyst is obtained which is kept in a dry and inert atmosphere prior to use. Its content of rhenium metal is 3% by weight.

Use in Metathesis

The 10 g of catalyst prepared hereinabove are charged into the same apparatus as that described in Example 1. Liquid propylene is injected at a flow rate of 43.8 g/h, at a temperature of 35° C. and at a pressure of 3.5 MPa. Under these conditions, 23.8% of propylene is converted.

EXAMPLE 3 (COMPARATIVE)

Preparation of the Catalyst

A new batch of catalyst is prepared as in Example 1, except that 9.61 g alumina is used and that the impregnation step with the niobium compound is omitted. The rhenium impregnation step and also the drying phase and final calcination phase are identical to those described in Example 1. Thus, 10 g of activated catalyst is obtained which is kept in a dry and inert atmosphere prior to use. Its content of rhenium metal is 3% by weight.

Use in Metathesis

The 10 g of catalyst prepared hereinabove is charged into the same apparatus as that described in Example 1. Liquid propylene is injected at a flow rate of 43.8 g/h, at a temperature of 35° C. and at a pressure of 3.5 MPa. Under these conditions, 7.1% of propylene is converted.

This example shows the poorer activity of a prior art catalyst.

EXAMPLE 4 (COMPARATIVE)

Preparation of the Catalyst

A new batch of catalyst is prepared as in Example 1, except that 8.96 g alumina is used and that the impregnation step with the niobium compound is omitted. In the rhenium impregnation step a solution is used which is obtained by diluting 0.61 ml of the concentrated solution of perrhenic acid in 5 ml water. After drying in a drying oven at 120° C. for one night, the catalyst is then calcined in a current of methane combustion gas at a temperature of 750° C. for 1 hour. During the subsequent cooling period, a current of dry nitrogen is substituted for the current of air. 10 g of activated catalyst is thus obtained which is kept in a dry and inert atmosphere prior to use. Its content of rhenium metal is 8% by weight.

Use in Metathesis

The 10 g of catalyst prepared hereinabove are charged into the same apparatus as that described in Example 1. Liquid propylene is injected at a flow rate of 43.8 g/h, at a temperature of 35° C. and at a pressure of 3–5 MPa. Under these conditions, 22.6% of propylene is converted.

This example, in comparison with Examples 1 and 2, shows that a prior art catalyst containing 8% rhenium is less active than a catalyst modified with niobium oxide according to the invention which contains only 3% of rhenium.

EXAMPLE 5

Preparation of the Catalyst

A cubic gamma alumina with a specific surface area of 184 m$^2$/g and a pore volume of 0.67 ml/g is calcined at 300° C. in air. After cooling at ambient temperature, this alumina is impregnated with a solution of 3.23 g of pentaethoxytantalum in 5 ml anhydrous ethanol. After 30 minutes of contact at ambient temperature, the solid obtained is dried in a drying oven at 120° C. for one night. It is then calcined in a current of air at about 20 l/h at a temperature of 500° C. for 2 hours. A solution is prepared for impregnating the rhenium by diluting 0.23 ml of a concentrated aqueous solution of perrhenic acid containing 54.08 % by weight of rhenium (specific mass: 2.417 g/ml) in 5 ml water. This solution is impregnated onto the previously calcined solid. After 30 minutes of contact at ambient temperature, the solid obtained is dried in a drying oven at 120° C. for one night. It is then calcined in a current of air (about 20 l/h), dried by passing through molecular sieve bed, at a temperature of 550° C. for 2 hours. During the subsequent cooling period, a current of dry nitrogen is substituted for the current of air. 10 g of activated catalyst is thus obtained which is kept in a dry and inert atmosphere prior to use. It content of tantalum oxide is 18.3 % by weight and its content of rhenium metal is 3% by weight.

Use in Metathesis

The 10 g of catalyst prepared hereinabove is charged into the same apparatus as that described in Example 1. Liquid propylene is injected at a flow rate of 43.8 g/h, at a temperature of 35° C., and at a pressure of 3.5 MPa. Under these conditions, 12.9% of the propylene is converted.

We claim:

1. A process for metathesis of olefins, comprising subjecting olefins to effective conditions in the presence of a catalyst, wherein the catalyst comprises a support containing at least 75% by weight of alumina, 0.01 to 20% by weight of rhenium in oxide form and 0.01 to 30% by weight of at least one oxide of niobium or tantalum.

2. A process according to claim 1, wherein the catalyst is obtained from a catalytic composition comprising at least one porous support containing at least 75% by weight of alumina, a compound of niobium or tantalum, and at least one rhenium compound, said composition being activated in a non-reducing atmosphere.

3. A process according to claim 1, wherein at least one alkali metal or alkaline earth metal is present in the catalyst.

4. A process according to claim 2, in which the catalyst contains a niobium compound which is a halide, oxyhalide, alkoxide, hydrated oxide complexed with oxalic acid, hydrated oxides complexed with tartaric acid or an ammonium salt of said oxalic or tartaric acid.

5. A process according to claim 2, wherein the catalyst contains a tantalum compound which is a halide, oxyhalide, alkoxide, hydrated oxide complexed with oxalic acid, hydrated oxides complexed with tartaric acid or an ammonium salt of said oxalic or tartaric acid.

6. A process according to claim 1, wherein the rhenium compound is rhenium heptoxide, ammonium perrhenate or perrhenic acid.

7. A process according to claim 1, wherein the porous support is alumina with a porosity which is at least equal to 0.1 ml/g and with a surface area which is at least equal to 10 m²/g.

8. A process according to claim 1, wherein the catalyst is prepared by introducing onto the support the niobium or tantalum, and then by introducing the rhenium compound.

9. A process according to claim 1, wherein the metathesis reaction is carried out in liquid phase at a temperature of between 0° and 200° C., and at a pressure which is at least equal to the vapor pressure of the reaction medium at the reaction temperature.

10. A process according to claim 1, wherein the olefins in the metathesis reaction are linear olefins or cyclic olefins.

11. A process for metathesis of olefins, comprising subjecting olefins to effective conditions in the presence of a catalyst, wherein the catalyst comprises a support containing alumina, a catalytically effective amount of rhenium in oxide form and a catalytically effective amount of at least one oxide of niobium or tantalum.

12. A process according to claim 1, wherein the catalyst is prepared from aqueous solutions of compounds of niobium or tantalum.

13. A process according claim 12, in which the catalyst contains a niobium compound which is a halide, oxyhalide, alkoxide, hydrated oxide complexed with oxalic acid, hydrated oxides complexed with tartaric acid or an ammonium salt of said oxalic or tartaric acid.

14. A process according claim 12, wherein the catalyst contains a tantalum compound which is a halide, oxyhalide, alkoxide, hydrated oxide complexed with oxalic acid, hydrated oxides complexed with tartaric acid or an ammonium salt of said oxalic or tartaric acid.

15. A process according to claim 1, wherein the catalyst contains an oxide of niobium.

16. A process according to claim 1, wherein the catalyst contains an oxide of tantalum.

* * * * *